United States Patent
Foreman et al.

(10) Patent No.: US 6,478,807 B1
(45) Date of Patent: Nov. 12, 2002

(54) PRE-FORMED EXPANDABLE MEMBER HAVING GROOVES

(75) Inventors: Philip C. Foreman, San Jose, CA (US); Timothy A. Limon, Cupertino, CA (US); Richard J. Saunders, Redwood City, CA (US); Björn G. Svensson, Morgan Hill, CA (US); Gregory W. Teaby, II, Sunnyvale, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 391 days.

(21) Appl. No.: 09/590,478

(22) Filed: Jun. 8, 2000

(51) Int. Cl.$^7$ .............................................. A61M 29/00
(52) U.S. Cl. ...................................... 606/194; 606/108
(58) Field of Search ................................ 606/194, 192, 606/195, 198, 108; 604/101.02, 96.01, 101.01, 101.03, 101

(56) References Cited

U.S. PATENT DOCUMENTS

| | | |
|---|---|---|
| 2,701,559 A | 2/1955 | Cooper |
| 4,199,646 A | 4/1980 | Hori et al. |
| 4,733,665 A | 3/1988 | Palmaz |
| 4,880,683 A | 11/1989 | Stow |
| 5,078,720 A | 1/1992 | Burton et al. |
| 5,100,429 A | 3/1992 | Sinofsky et al. |
| 5,108,416 A | 4/1992 | Ryan et al. |
| 5,156,911 A | 10/1992 | Stewart |
| 5,158,548 A | 10/1992 | Lau et al. |
| 5,242,399 A | 9/1993 | Lau et al. |
| 5,300,023 A * | 4/1994 | Lowery et al. ............. 604/271 |
| 5,344,426 A | 9/1994 | Lau et al. |
| 5,360,401 A | 11/1994 | Turnland |
| 5,387,450 A | 2/1995 | Stewart |
| 5,412,035 A | 5/1995 | Schmitt et al. |
| 5,445,646 A | 8/1995 | Euteneuer et al. |
| 5,514,154 A | 5/1996 | Lau et al. |
| 6,123,712 A * | 9/2000 | Di Caprio et al. ........... 606/108 |
| 6,200,325 B1 * | 3/2001 | Durcan et al. ......... 604/101.05 |
| 6,383,212 B2 * | 5/2002 | Durcan et al. .............. 606/108 |
| 6,391,002 B1 * | 5/2002 | Kokish .................. 604/103.06 |
| 6,419,685 B2 * | 7/2002 | Di Caprio et al. .......... 606/192 |

FOREIGN PATENT DOCUMENTS

| | | |
|---|---|---|
| EP | 0 834 293 A1 | 4/1998 |
| EP | 0 974 315 | 1/2000 |
| EP | 1132059 | * 12/2001 |
| FR | 2 753 907 A1 | 10/1996 |
| WO | WO 95/33422 | 12/1995 |
| WO | WO 98/07390 | 2/1998 |

* cited by examiner

Primary Examiner—Teresa Walberg
Assistant Examiner—Vinod D Patel
(74) Attorney, Agent, or Firm—Fulwider Patton Lee & Utecht, LLP

(57) ABSTRACT

A catheter assembly is provided for use in delivering and implanting a stent in a body lumen, such as in a coronary artery. An elongated catheter body includes an expandable member or balloon having a folded configuration and an expanded configuration wherein a plurality of pre-formed grooves extending generally circumferentially around the balloon when the balloon is in its folded configuration. An intravascular stent is removably crimped over the balloon and is at least partially retained on the balloon by the grooves. Upon inflation of the balloon, the grooves will flatten out thereby releasing the stent and allowing the stent to expand radially outwardly into contact with the body lumen or coronary artery.

34 Claims, 4 Drawing Sheets

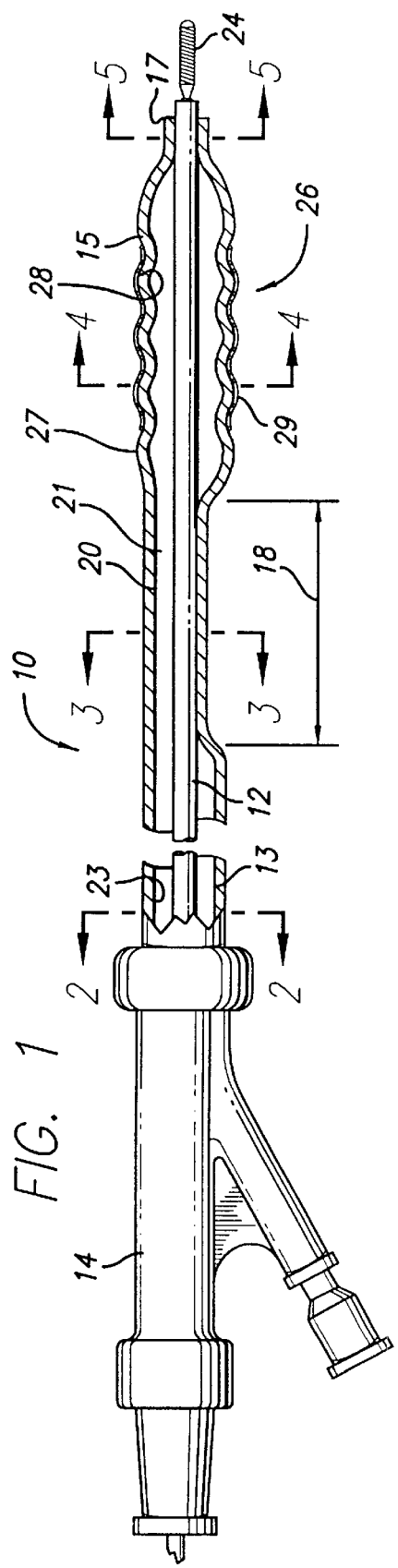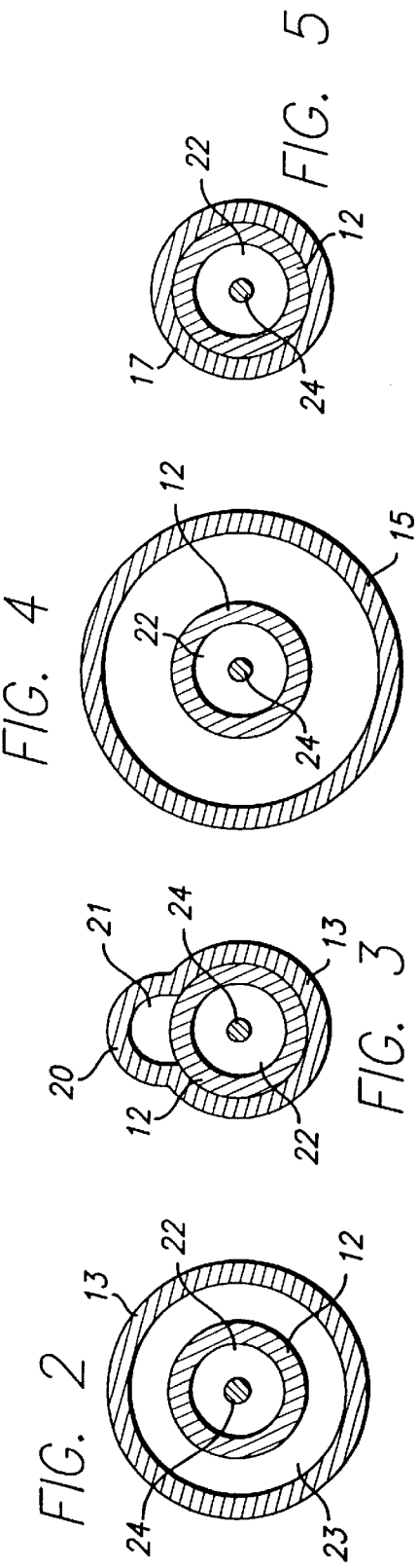

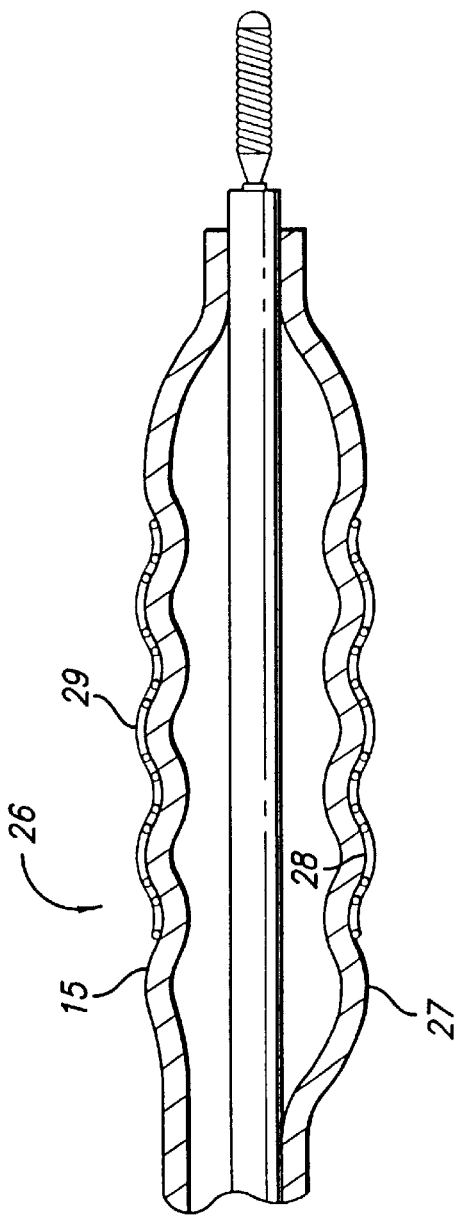
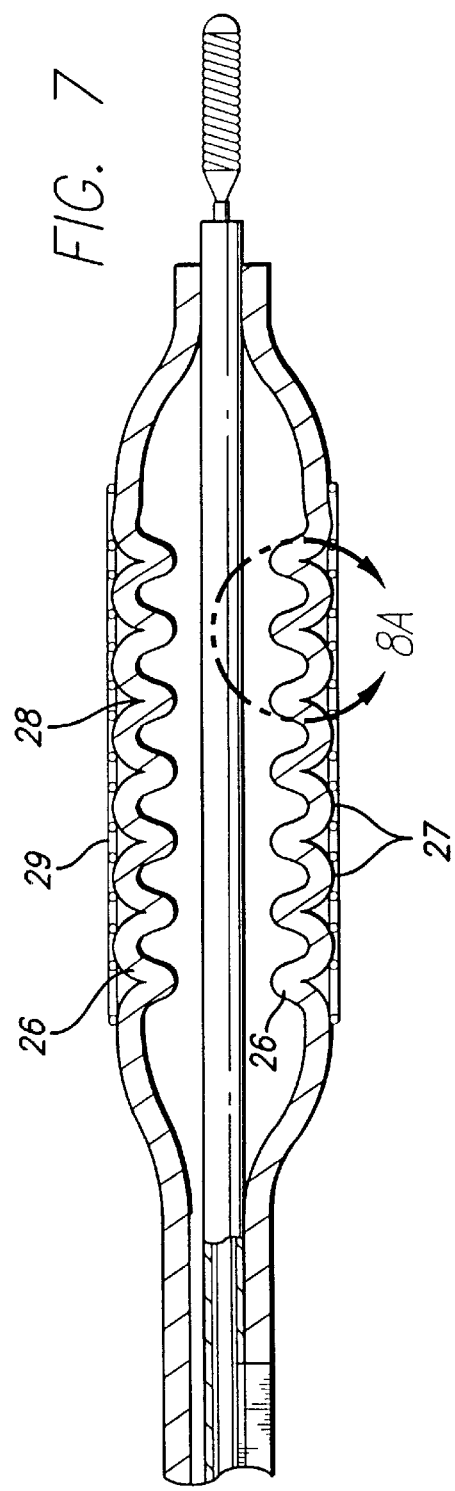

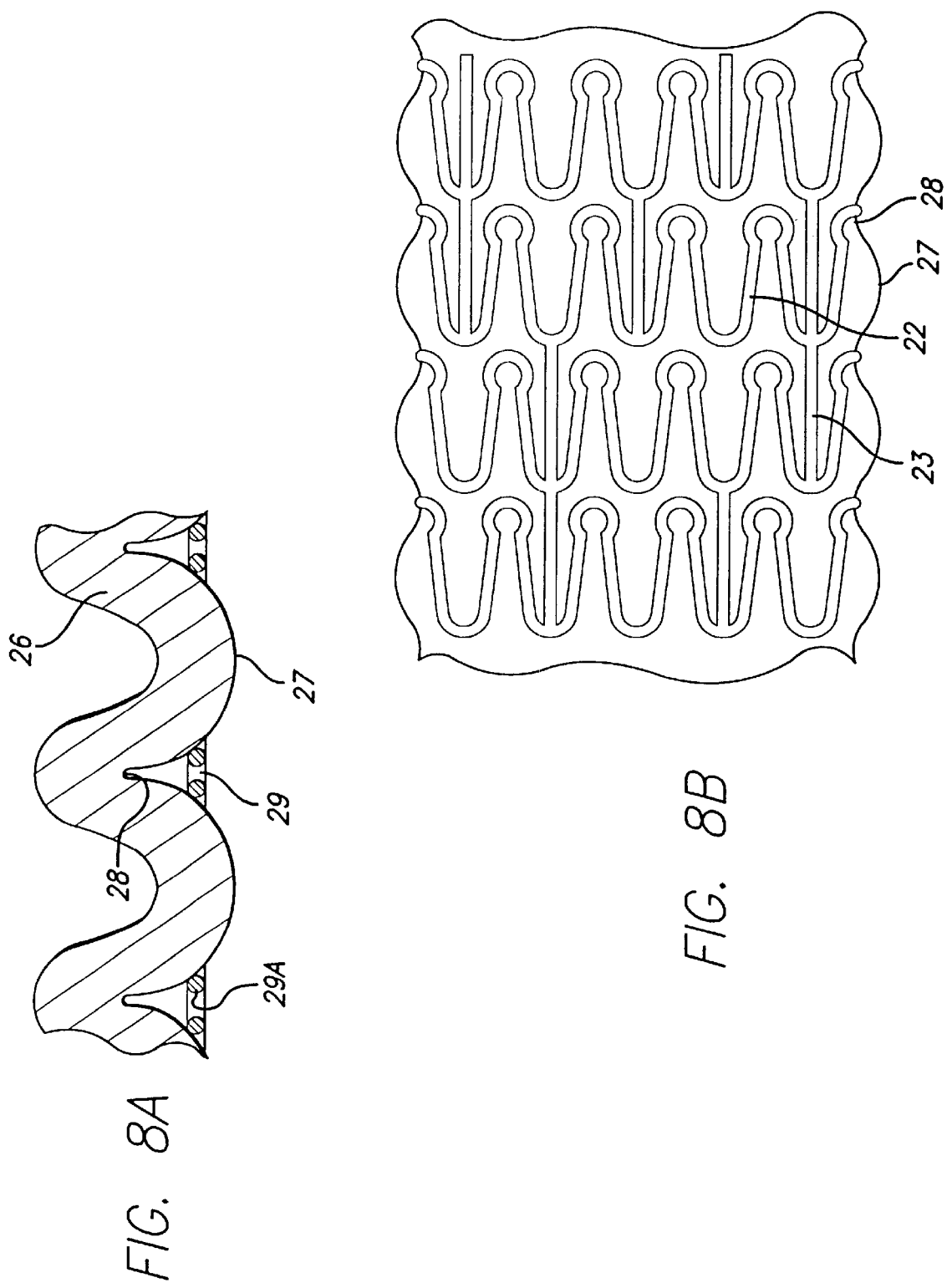

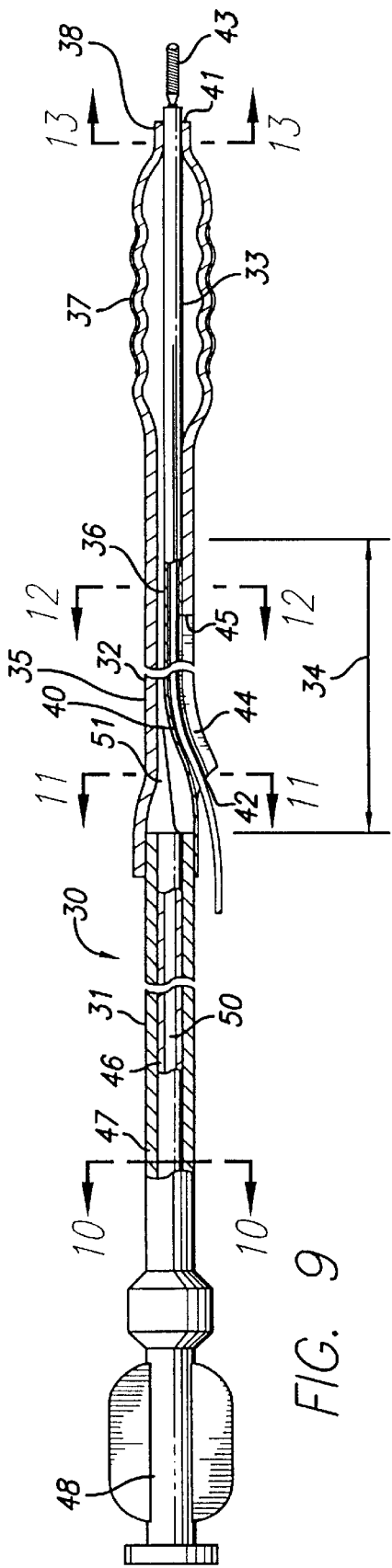
FIG. 9
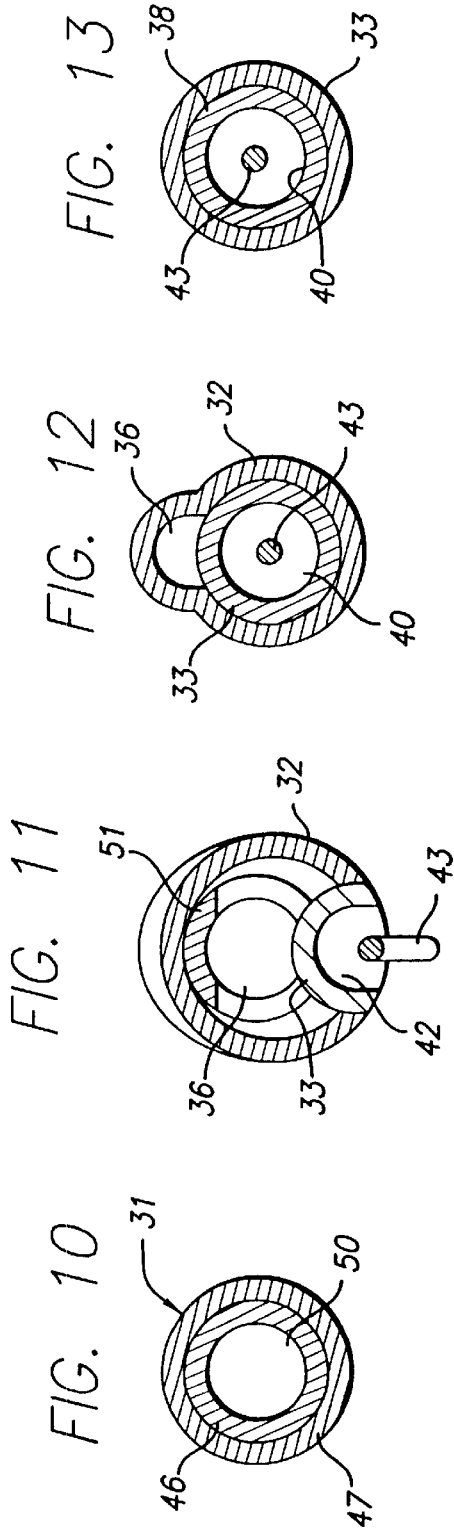
FIG. 10
FIG. 11
FIG. 12
FIG. 13

PRE-FORMED EXPANDABLE MEMBER HAVING GROOVES

BACKGROUND OF THE INVENTION

This invention generally relates to intravascular catheters, such as balloon catheters, for use in the delivery of intravascular stents for repairing body lumens, and more particularly for repairing coronary arteries and peripheral vessels.

It is well known that percutaneous transluminal angioplasty (PTCA) is a widely used procedure for the treatment of coronary heart disease wherein a balloon dilatation catheter is advanced into the patient's coronary artery and the balloon on the distal portion of the catheter is inflated within a stenotic region of the patient's artery to open up the arterial passageway and thereby increase the blood flow therethrough. It is also well know that subsequent to PTCA procedures, arteries can abruptly close (abrupt and threatened closure), or more commonly, restenosis can occur over time where the artery tends to re-close due to the growth of cells around the area treated by the PTCA procedure.

A wide variety of repair devices, including intravascular stents, have been used to prevent abrupt or threatened closure and to reduce the likelihood of the development of restenosis. There are numerous intravascular stents manufactured and sold throughout the world with varying degrees of success in reducing the likelihood of the development of restenosis.

Presently, hundreds of thousands of stents are implanted in the coronary arteries and peripheral vessels of patients having some form of vascular disease. One of the problems associated with implanting stents is the ability to deliver the stent on a catheter without the stent coming off the catheter until it is desired to be implanted. In other words, the stent comes off the balloon portion of the catheter prior to reaching the target site, and washes downstream through the patient's vasculature.

There have been several solutions to prevent the stent from prematurely coming off the catheter, such as a retractable sheath that covers the stent, or collars at either end of the stent to prevent stent movement on the balloon portion of the catheter. Neither of these prior art solutions has been effective for various reasons. Both sheaths and collars can increase rigidity in the distal end of the catheter where flexibility is essential. Further, sheaths and collars may increase the overall profile of the device, also undesirable.

What has been needed, and heretofore not available, is a balloon catheter that is configured to retain a stent on the balloon portion of the catheter during delivery through tortuous coronary arteries, yet maintain flexibility and allow the stent to expand easily away from the balloon portion of the catheter when it is implanted in the vessel. The present invention satisfies these and other needs.

SUMMARY OF THE INVENTION

The present invention is directed to an elongated intravascular catheter having an expandable balloon capable of removably retaining a stent thereon.

The catheter of the present invention has an elongated catheter body which includes a proximal end and a distal end and generally has at least one lumen extending therethrough. Typically, there are two lumens extending coaxially through the catheter, one lumen for receiving a guide wire and the other lumen for transmitting inflation fluid to an expandable member, or balloon, located at the distal end of the catheter. The expandable member has a folded configuration and an expanded configuration and expands when the inflation fluid is injected through the catheter and into the interior of the balloon. The balloon has a plurality of preformed grooves extending generally circumferentially around the balloon when the balloon is in the folded configuration. When the balloon is expanded, the grooves flatten out and essentially disappear. When the balloon is deflated, it is not necessary that the preformed grooves re-form, only that they not prevent the balloon from completely deflating so that the catheter and balloon portion can be withdrawn from the patient without catching on any part of the vasculature.

The grooves in the balloon can be further defined as having peaks and valleys, wherein the distance from the peaks to the valleys typically is in the range of about 0.01 mm to 1.5 mm. The grooves generally are uniformly spaced along the longitudinal axis of the balloon, and can define a circumferential or helical pattern along the balloon as well.

In one embodiment of the invention, a catheter assembly is used for delivering and implanting a stent in a body lumen, such as in the coronary arteries or in peripheral vessels. The catheter assembly includes an elongated catheter body having a proximal end and a distal end and typically includes an inflation lumen and a guide wire lumen. The expandable member, or balloon portion of the catheter, has a folded configuration and an expanded configuration and is in fluid communication with the inflation lumen. There are a plurality of pre-formed grooves extending generally circumferentially around the balloon when the balloon is in its folded configuration. The preformed grooves are typically uniformly spaced along the length of the balloon. An intravascular stent is removably crimped over the balloon and is at least partially retained thereon by the grooves as the stent closely follows the contour of the grooves. Typically, stents are comprised of metallic tubes having deformable metal that will conform to the grooves along the length of the balloon.

In another embodiment of the invention, a catheter assembly is used for delivering and implanting a stent in a body lumen, such as in the coronary arteries or in peripheral vessels. The catheter assembly includes an elongated catheter body having a proximal end and a distal end and typically includes an inflation lumen and a guide wire lumen. The expandable member or balloon portion of the catheter has a folded configuration and an expanded configuration and is in fluid communication with the inflation lumen. There are a plurality of preformed grooves extending generally circumferentially around the balloon when the balloon is in its folded configuration. An intravascular stent is removably crimped over the balloon and is at least partially retained thereon by the grooves extending within the matrix of the stent. Typically, intravascular stents are comprised of metallic tubes having a matrix-like structure with a number of openings or holes through the tubular structure. The grooves of the balloon are positioned so that at least some of the grooves extend into the apertures as the stent is crimped onto the balloon.

When the balloon is inflated, the stent expands radially outwardly and the grooves flatten out thereby releasing the stent which is then implanted into the vessel. The balloon is then deflated and the catheter and balloon withdrawn from the patient's vasculature. The grooves of the balloon define an outer surface which can be identified as peaks and valleys. The outward radial distance between a peak and a valley can vary and typically is in the range of about 0.01 mm to 1.5 mm. In this embodiment, the grooves generally are uniformly spaced along the length of the balloon and can define a helical pattern as well.

The balloon of the present invention can be formed from a polymeric material, such as for example, nylon, PEBAX (polyamide block co-polymer) polyethylene, polyethylene terephthalate and other relatively inelastic polymers and other materials.

The catheter assembly of the present invention can include catheters of the rapid-exchange type in which the guide wire lumen extends through a portion of the catheter, typically through the distal portion of the catheter and having a guide wire exit port located on the catheter proximal to the balloon. The catheter assembly of the present invention also can be of the over-the-wire type, in which the guide wire lumen extends through the catheter from its proximal end to its distal end.

The improvements of the present invention are applicable to a wide range of elongated intravascular catheters which are at least 90 cm in length and which are percutaneously introduced and advanced within a patient's vascular system, such as the coronary arteries. It is particularly suitable in all types of stenting procedures and can be used with a wide variety of intravascular stents. These and other advantages of the invention will become more apparent from the following detailed description of the invention when taken in conjunction with the accompanying exemplary drawings.

BRIEF DESCRIPTION OF THE DRAWINGS

FIG. 1 is an elevational view, partially in section, of a balloon dilatation catheter embodying features of the invention.

FIG. 2 is a transverse cross-sectional view of the catheter shown in FIG. 1 taken along the lines 2—2.

FIG. 3 is a transverse cross-sectional view of the catheter shown in FIG. 1 taken along the lines 3—3.

FIG. 4 is a transverse cross-sectional view of the catheter shown in FIG. 1 taken along the lines 4—4.

FIG. 5 is a transverse cross-sectional view of the catheter shown in FIG. 1 taken along the lines 5—5.

FIG. 6 is a partial cross-sectional view depicting the balloon portion of the catheter embodying features of the invention.

FIG. 7 is a partial cross-sectional view depicting the balloon portion of the catheter embodying features of the invention.

FIG. 8A is an enlarged cross-sectional view of a portion of the balloon portion of the catheter depicting the balloon grooves at least partially inserted within holes in the stent.

FIG. 8B is a partial cross-sectional view depicting a stent having rings and links mounted on the balloon portion of the catheter.

FIG. 9 is an elevational view, partially in section, of another catheter embodying features of the invention.

FIG. 10 is a transverse cross-sectional view of the catheter shown in FIG. 6 taken along the lines 10—10.

FIG. 11 is a transverse cross-sectional view of the catheter shown in FIG. 6 taken along the lines 11—11.

FIG. 12 is a transverse cross-sectional view of the catheter shown in FIG. 6 taken along the lines 12—12.

FIG. 13 is a transverse cross-sectional view of the catheter shown in FIG. 6 taken along the lines 13—13.

DETAILED DESCRIPTION OF THE PREFERRED EMBODIMENTS

The present invention relates to a balloon catheter for use in the delivery and implantation of an intravascular stent. More specifically, the invention relates to a balloon structure that enhances the ability to hold a stent on the balloon during delivery, yet easily releases the stent as the balloon is expanded into contact with a coronary artery or other vessel. The invention is applicable to a wide range of balloon catheters, including over-the-wire and rapid-exchange type catheters as will be herein described.

FIGS. 1–5 schematically illustrate an over-the-wire stent delivery catheter embodying features of the invention. The catheter 10 includes an elongated catheter shaft 11 which has an inner tubular member 12, an outer tubular member 13 disposed about the inner tubular member and an adapter 14 secured to the proximal ends of the inner and outer tubular members. A relatively inelastic, expandable member or inflatable balloon 15 formed integral with the outer tubular member 13 and a distal skirt 17 secured to the distal end of the inner tubular member 12. Alternatively, the balloon 15 may be formed from different material and be secured to the outer tubular member 13.

As shown in FIGS. 1 and 3, the distal portion of the outer tubular members 13 in part takes the shape of and is secured to the exterior of the inner tubular member 12 along the length 18. The unsecured portion 20 of the outer tubular member 13 along the length 18 forms with the inner tubular member 12 an inflation lumen 21 which is in fluid communication with the interior of the balloon 15. The inner lumen 22 of the inner tubular member 12 extends parallel to the inflation lumen 21 along the length 18. As best shown in FIG. 3, the transverse dimension of the catheter shaft 11 along the length 18 in the vertical direction is substantially larger than the transverse dimension of the catheter shaft in the horizontal direction along said length.

The proximal portion of the catheter shaft 11, as shown in FIGS. 1–3, is conventional where the outer tubular member 13 is disposed about but is unsecured to the inner tubular member 12 and defines with the inner tubular member an annular inflation lumen 23 which is in fluid communication with the inflation lumen 21 in the distal portion of the catheter shaft.

In keeping with the invention, and as depicted more clearly in FIGS. 6–8, the balloon 15 has a plurality of grooves 26 spaced along the longitudinal length of the balloon. The grooves have peaks 27 and valleys 28, wherein the distance of the peaks from the valleys is in the range of about 1.01 mm to 1.5 mm. In one embodiment of the invention, as shown in FIG. 6, an intravascular stent 29 is mounted on the balloon and is tightly crimped thereon so that the stent follows the peaks and valleys. In this embodiment, the stent ends should be positioned so that they are in a valley which will help protect the stent ends as the stent is delivered through a tortuous vessel, such as a coronary artery.

In another embodiment of the invention, as shown more clearly in FIGS. 7, 8A and 8B, an intravascular stent 29 is mounted on the balloon so that the peaks 27 project at least part way into apertures or holes 29A in the stent. Preferably, the peaks extend only part way into the apertures and not all the way through to the stent outer surface. This embodiment is particularly useful when used with stent designs having rings and links so that the peaks can project at least part way into the spaces between rings. A typical stent having rings 22 and links 23 is shown in FIG. 8B and peaks 27 project at least part way into the space between the rings.

The balloon grooves 26 are preformed during the balloon molding or blowing process and typically extend circumferentially around the balloon and are uniformly spaced around the axis of the balloon. It is contemplated that the grooves could be helical or spiral along the length of the balloon as well. It is generally desirable to firmly crimp the stent in a known manner on the balloon portion of the catheter, such stents typically being formed from a metal tube that is laser cut to form a pattern in the stent including apertures or holes 29A. As the stent is crimped onto the balloon catheter, the peaks 27 project into the holes 29A providing a gripping force so that the stent is less likely to move longitudinally on the balloon during the delivery process through tortuous vessels, such as the coronary arteries. Thus, the stent remains firmly crimped onto the balloon until the stent is delivered at the target site where it is expanded and implanted in the vessel in a known manner as is described below.

In a typical angioplasty and stenting procedure, a balloon dilatation catheter is advanced along with a guide wire through a guiding member (not shown) until the catheter and guide wire reach the distal end of the guide catheter which is positioned at the ostium of the coronary arteries. Thereafter, typically the guide wire is advanced past the stenosed area (target site) and the catheter is advanced over the guide wire until the balloon is positioned at the target site. The balloon is then inflated in a conventional manner and the artery wall remodeled to increase blood flow in the area. The catheter is removed by withdrawing it over the in-place guide wire, which remains positioned so that the distal end of the guide wire is distal to the target site. The patient is now ready for the stenting procedure in accordance with the present invention.

The use of the stent delivery catheter shown in FIGS. 1–5 generally may follow conventional stent delivery practices with over-the-wire-type catheters. The already in-place guide wire 24 is frontloaded into the inner lumen 22 of the inner tubular member 12 and the catheter 10 is advanced over the guide wire and through the guiding catheter. The catheter is advanced over the guide wire, which is being held in position, until the balloon 15 on the catheter is properly disposed within the target area, so that the stent can be implanted. Up to this point, the stent 29 is firmly held in place by grooves 26 as previously described, as the catheter is advanced through the tortuous coronary arteries. Once the balloon and stent are positioned within the target area, the balloon is inflated which in turn radially expands the stent into contact with the coronary artery wall. As the balloon expands, the grooves flatten out and essentially release the stent from the balloon. Thereafter, the stent remains implanted in the coronary artery. After stenting, the balloon is deflated and the catheter and the guide wire may be withdrawn from the patient. Typically, the guide wire 24 is left in the patient for subsequent procedures, such as implanting a second stent, or using a high-pressure balloon to more firmly implant the first stent. Other procedures may also be performed prior to removing the guide wire and guiding catheter from the patient.

FIGS. 9–13 schematically illustrate another stent delivery catheter 30 embodying features of the invention which is configured for rapid exchange. The structure of the most distal portion of the catheter shaft 31 is quite similar to the embodiment shown in FIGS. 1–5 in that the distal section of the catheter shaft 31 includes an outer tubular member 32 which is disposed about an inner tubular member 33 and which in part takes the shape of and is secured to the exterior of the inner tubular member along a length 34 of the distal shaft. An unsecured portion 35 of the outer tubular member 32 forms an inflation lumen 36 which is in fluid communication with the relatively inelastic expandable member or balloon 37. In this embodiment, the outer tubular member 32 and the balloon 37 are formed in a unitary construction. The distal skirt 38 of the balloon 37 is secured to the distal end of the inner tubular member 33.

Guide wire receiving inner lumen 40 extends proximally within the inner tubular member 33 from a distal guide wire port 41 in the distal end of the inner tubular member to a proximal guide wire port 42. A guide wire 43 is slidably disposed within the inner lumen 40 and extends out both the distal port 41 and the proximal port 42. A slit 44 may be provided in the secured sections of the inner and outer tubular members 33 and 32 respectively and it extends distally from the proximal guide wire port 42 to a location 45 proximal to the balloon 37 to facilitate separation of the guide wire 43 and the catheter shaft 32 when replacing catheter 30 with another catheter, such exchanges being generally known in the art. The proximal guide wire port 42 is located at least about 5 cm but not more than about 45 cm from the distal end of the catheter.

The proximal portion of the catheter shaft 31 has a high strength inner tubular member 46, e.g., hypotubing, with a tightly fitting outer plastic jacket or coating 47. An adapter 48 is secured to the proximal end of the catheter shaft 31 to direct inflation fluid through the inner lumen 50 in the high strength tubular member 46 and the inflation lumen 36 between the inner tubular member 33 and the unsecured portion of the outer tubular member 32 to the interior of balloon 37. The distal extremity 51 of the high strength tubular member 46 is tapered to facilitate extension into the proximal end of the inflation lumen 36 where it is secured by suitable means such as an adhesive or by heat shrinking the proximal end of the outer tubular member about the tapered extremity 51. The high strength tubular member may be formed of stainless steel or a NiTi alloy, particularly a NiTi alloy with pseudoelastic properties.

As described for the over-the-wire catheter as shown in FIGS. 1–5, the rapid-exchange catheter shown in FIGS. 9–13 also feature embodiments of the invention, as shown in FIGS. 6–8. As previously described, the embodiments shown in FIGS. 6–8 can be incorporated in the rapid-exchange catheter shown in FIGS. 9–13. The procedure for stenting with a rapid-exchange catheter embodying the invention is described below.

There are at least two modes of inserting the catheter 30 of this embodiment into the patient's coronary anatomy. The first method is for the most part the same as in the prior embodiment, namely, the guide wire 43 is preloaded into the short guide wire receiving inner lumen 40 of the inner tubular member 33 and both are advanced through a guiding catheter (not shown) previously disposed within the patient's arterial system with the distal end of the guiding catheter seated within the ostium of a coronary artery. The second mode, frequently called the "bare wire" technique, involves first advancing a guide wire 43 through and out the guiding catheter until the distal extremity of the guide wire is positioned within the patient's coronary artery across the lesion to be dilated. After the lesion is dilated with a suitable dilatation catheter, the stent catheter 30 is inserted by taking the proximal end of the guide wire 43, which is outside the patient and backloading, i.e., inserting it into the short inner lumen 40 of the inner tubular member 33 and advancing the catheter until the guide wire exits the guide wire port 42. The proximal end of the guide wire 43 is held in place and the catheter 30 is advanced over the guide wire through the patient's vascular system until the stent and balloon 37 are positioned across the target area. The target area is stented using the rapid-exchange catheter in the same manner as described for the over-the-wire catheter. In other words, the balloon 37 is inflated which in turn radially expands the stent into contact with the coronary artery. As the balloon expands, grooves 26 flatten out and no longer hold the stent on the balloon. After the lesion has been stented, the balloon is deflated and the catheter is removed from the patient's artery. If other treatments are necessary, the catheter 30 is slidably withdrawn over the guide wire 43, leaving the guide wire in place so that other catheters can be advanced over the in-place guide wire in a similar manner without the need for exchange wires or guide wire extensions, thereby significantly reducing the overall time for the procedure.

The various components of the catheters and guide wires of the invention can be formed from a wide variety of conventional materials. The catheter shaft, including the inner and outer tubular members may be made from polymeric materials such as polyethylene, polyamide, polyvinyl chloride, polyester (e.g. Hytrel® which is available from DuPont), polyetheretherketone (e.g. Grade 382G from Victrex U.S.A.) and other suitable polymeric materials. The hypotubing may be formed of stainless steel or NiTi superelastic alloy material, such as described previously. The balloon may be made from polyethylene, polyethylene terephthalate and other relatively inelastic polymers and other materials.

The dimensions of the catheters generally follow the dimensions of conventional intravascular catheters. For coronary use the length is typically about 135 cm and the maximum outer diameter of the outer tubular member is about 0.02 to about 0.06 inch (0.51–1.452 mm). The transverse shape of the proximal section of the catheter shaft may be circular, oviform or elliptical.

While the invention has been described herein primarily in terms of certain preferred embodiments, the invention may be employed in a wide variety of embodiments. Additionally, modifications and improvements can be made to the invention without departing from the scope thereof. Although individual features of embodiments of the invention may be shown in some of the drawings and not in others, those skilled in the art will recognize that individual features of one embodiment of the invention can be combined with any or all the features of another embodiment.

What is claimed:

1. An intravascular catheter, comprising:
    an elongated catheter body having a proximal end and a distal end and at least one lumen extending therein;
    an expandable member having a folded configuration and an expanded configuration and positioned proximate the distal end of the catheter, the expandable member being in fluid communication with the at least one lumen; and
    a plurality of preformed grooves extending circumferentially around the expandable member when the expandable member is in the folded configuration.
2. The catheter of claim 1, wherein the grooves provide an irregular surface when the expandable member is in the folded configuration.
3. The catheter of claim 1, wherein the grooves are defined by peaks and valleys.
4. The catheter of claim 3, wherein the peaks of the grooves define an outer surface of the expandable member.
5. The catheter of claim 4, wherein the radial outward distance from the peaks to the valleys is in the range of about 0.01 mm to 1.5 mm.
6. The catheter of claim 1, wherein the grooves are uniformly spaced long the expandable member.
7. The catheter of claim 1, wherein the grooves define a helical pattern along the expandable member.
8. The catheter of claim 1, wherein each of the grooves define an annulus on the expandable member.
9. The catheter of claim 1, wherein the grooves substantially flatten when the expandable member is in the expanded configuration.
10. The catheter of claim 1, wherein the expandable member is formed from a polymeric material taken from the group of materials consisting of polyethylene, polyethylene terephthalate and other relatively inelastic polymers and other materials.
11. The catheter of claim 1, wherein the grooves are preformed when the expandable member is blow-molded.
12. The catheter of claim 1, wherein the catheter and the expandable member are formed from the same polymeric material.
13. The catheter of claim 1, wherein the catheter includes a guide wire lumen extending from the catheter proximal end to the catheter distal end.
14. The catheter of claim 1, wherein the catheter includes a guide wire lumen extending from the catheter proximal end to a point proximal of the catheter distal end.
15. The catheter of claim 1, wherein the expandable member is configured to receive an intravascular stent.
16. The catheter of claim 1, wherein the expandable member is blow-molded from the catheter body.
17. The catheter of claim 1, wherein the expandable member is attached to the catheter body using an adhesive.
18. A catheter assembly for use in delivering and implanting a stent in a body lumen, comprising:
    an elongated catheter body having a proximal end and a distal end and at least one lumen extending therein;
    an expandable member having a folded configuration and an expanded configuration and positioned proximate the distal end of the catheter, the expandable member being in fluid communication with the at least one lumen; and
    a plurality of preformed grooves extending circumferentially around the expandable member when the expandable member is in the folded configuration; and
    a stent removably crimped over the expandable member and at least partially retained thereon by the grooves.
19. The catheter assembly of claim 18, wherein the grooves provide an irregular surface when the expandable member is in the folded configuration.
20. The catheter assembly of claim 18, wherein the grooves are defined by peaks and valleys.
21. The catheter assembly of claim 20, wherein the peaks of the grooves define an outer surface of the expandable member.
22. The catheter assembly of claim 21, wherein the distance from the peaks to the valleys is in the range of about 0.01 mm to 1.5 mm.
23. The catheter assembly of claim 18, wherein the grooves are uniformly spaced along the expandable member.
24. The catheter assembly of claim 18, wherein the grooves define a helical pattern along the expandable member.
25. The catheter assembly of claim 18, wherein each of the grooves define an annulus on the expandable member.
26. The catheter assembly of claim 18, wherein the grooves substantially flatten when the expandable member is in the expanded configuration.
27. The catheter assembly of claim 18, wherein the expandable member is formed from a polymeric material taken from the group of materials consisting of polyethylene, polyethylene terephthalate and other relatively inelastic polymers and other materials.

28. The catheter assembly of claim 18, wherein the grooves are preformed when the expandable member is blow-molded.

29. The catheter assembly of claim 18, wherein the catheter and the expandable member are formed from the same polymeric material.

30. The catheter assembly of claim 1, wherein the catheter includes a guide wire lumen extending from the catheter proximal end to the catheter distal end.

31. The catheter assembly of claim 1, wherein the catheter includes a guide wire lumen extending from the catheter proximal end to a point proximal of the catheter distal end.

32. The catheter assembly of claim 1, wherein the expandable member is configured to receive an intravascular stent.

33. The catheter of claim 18, wherein the expandable member is blown from the catheter body.

34. The catheter of claim 18, wherein the expandable member is attached to the catheter body using an adhesive.

\* \* \* \* \*